United States Patent
Biering et al.

(10) Patent No.: US 7,470,655 B2
(45) Date of Patent: Dec. 30, 2008

(54) METHOD OF INACTIVATING PRIONS

(75) Inventors: Holger Biering, Grevenbroich (DE); Thomas Merz, Hilden (DE); Bernhard Meyer, Metmann (DE); Friedrich Von Rheinbaben, Monheim (DE)

(73) Assignee: Ecolab Inc., St. Paul, MN (US)

( * ) Notice: Subject to any disclaimer, the term of this patent is extended or adjusted under 35 U.S.C. 154(b) by 380 days.

(21) Appl. No.: 10/913,070

(22) Filed: Aug. 6, 2004

(65) Prior Publication Data
US 2006/0030505 A1    Feb. 9, 2006

(51) Int. Cl.
C11D 1/66    (2006.01)
C11D 3/39    (2006.01)
C11D 3/395    (2006.01)
B08B 3/04    (2006.01)

(52) U.S. Cl. .................. 510/372; 510/238; 510/421; 510/488; 134/42; 422/28

(58) Field of Classification Search ................ None
See application file for complete search history.

(56) References Cited

U.S. PATENT DOCUMENTS

| 6,214,366 B1 | 4/2001 | Prusiner et al. | |
| 6,322,802 B1 | 11/2001 | Prusiner et al. | |
| 6,419,916 B1 | 7/2002 | Prusiner et al. | |
| 6,479,454 B1 * | 11/2002 | Smith et al. | 510/503 |
| 6,506,416 B1 * | 1/2003 | Okauchi et al. | 424/615 |
| 6,517,855 B2 | 2/2003 | Prusiner et al. | |
| 6,540,960 B2 * | 4/2003 | Biering et al. | 422/28 |
| 6,719,988 B2 * | 4/2004 | Prusiner et al. | 424/405 |
| 6,720,355 B2 | 4/2004 | Prusiner et al. | |
| 2003/0073592 A1 * | 4/2003 | McDonnell et al. | 510/161 |
| 2003/0109405 A1 * | 6/2003 | Kellar et al. | 510/375 |
| 2004/0029755 A1 * | 2/2004 | Bragulla | 510/218 |
| 2004/0171507 A1 * | 9/2004 | Kellar et al. | 510/367 |
| 2005/0153854 A1 * | 7/2005 | Meyer et al. | 510/161 |

FOREIGN PATENT DOCUMENTS

| EP | 1454637 | 9/2004 |
| WO | WO01/54736 | 8/2001 |
| WO | WO02/083082 | 10/2002 |
| WO | WO03/031551 | 4/2003 |
| WO | WO03/031552 | 4/2003 |
| WO | WO03/031987 | 4/2003 |
| WO | WO03/064580 | 8/2003 |

OTHER PUBLICATIONS

B. Homlimann, D. Riesner and H. Kretzschmar; Walter de Gruyter. Berlin, New York, 2001, Task Force RK1. Die Variante der Creuzfeldt-Jacob-Krankheit (vCJK), Bundesgesundheitsblatt-Gesundheitsforschung—Gesunheitsschutz 45, 376-394 (2002).
G.E. McDonell, Prion Disease and Medical Devices, ASAOI J 46 (2000) S69-S72.
Homlimann, Leutwiler, Oberthur, Widmer, "Die chemische Desinfektion and Inaktivierung von Prionen", p. 381-388.
J. Bertram, M. Mielke et al., Inaktivierung und Entfernung von Prionen bei der Aufbereitung von Medizinprodukten, Bundesgesundheitblatt-Gesundheitsforschung-Gesundheitsschutz, 47, 36-40 (2004).
Thomas Raul Appel, Michael Wolff, Friedrich von Rheinbaben, Michael Heinzel. Detlev Riesner, "Heat stability of prion rods and recombinant prion protein in water, lipid and lipid—water mixtures", Journal of General Virology (2001), 82, 465-473, 9 pages.
Antloga K et al., "Prion Disease and Medical Devices", ASAOI Journal vol. 46 No. 6, 2000, pp. S69-S72, XP001092854 ISSN: 1058-2916.
Hauthal H G Et al., "Studies Concerning the Mechanism of Bleaching Activation", vol. 27, No. 3, May 1, 1990 pp. 187-193, XP000132520, ISSN: 0932-3414.
M. Baier, A. Schwarz, M. Mielke, "Activity of an alkaline 'cleaner' in the inactivation of the scrapie agent", 2004 The Hospital Infection Society, Elsevier Ltd.
World Health Organization, "WHO Infection Control Guidelines for Transmissible Spongiform Encephalopathies", p. 13, section 6.1, WHO/CDS/CSR/APH/2000.3, report of a WHO Consultation, Geneva, Switzerland, Mar. 23-26, 1999.

* cited by examiner

Primary Examiner—Gregory R Del Cotto
(74) Attorney, Agent, or Firm—Andrew D. Sorensen; Anneliese S. Mayer

(57) ABSTRACT

The invention pertains to a method of inactivating prions located on surfaces. In an embodiment, the invention pertains to a method of inactivating prions located on surfaces using a composition including a peracid. In an embodiment, the invention pertains to a method of inactivating prions located on surfaces using a composition including a peracid and a surfactant. The composition may comprise additional functional ingredients.

4 Claims, No Drawings

METHOD OF INACTIVATING PRIONS

FIELD OF THE INVENTION

The invention pertains to a method of inactivating prions located on surfaces. In an embodiment, the invention pertains to a method of inactivating prions located on surfaces using a composition including a peracid. In an embodiment, the invention pertains to a method of inactivating prions located on surfaces using a composition including a peracid and a surfactant. The composition may comprise additional functional ingredients.

BACKGROUND

Prions are proteinaceous infections particles free of nucleic acid. Prions are known to cause several brain diseases including kuru, Creutzfeldt-Jakob disease, Gerstmann-Straussler-Scheinker disease, and fatal familial insomnia in humans; scrapie in sheep; bovine spongiform encephalopathy (Mad Cow Disease) in cattle; transmissible mink encephalopathy in mink; chronic wasting disease in deer and elk; and feline spongiform encephalopathy in cats. These diseases lead to symptoms including dementia, ataxia, behavioral disturbances, dizziness, involuntary movement, and death. Prions can be transmitted by exposure to infected tissue and brain tissue, spinal cord tissue, pituitary tissue, and eye tissue in particular.

Prions are difficult to decontaminate using conventional chemical and physical methods. Many traditional chemical disinfectants are ineffective against prions, or have limited efficacy, including alcohol, ammonia, hydrogen peroxide, peracetic acid and boiling. Some traditional chemical and physical disinfectants have been shown to be variably effective including sodium hydroxide, guanidinium isothiocyanate (4M), autoclaving at at least 134° C. for at least one hour, and boiling in 3% sodium dodecyl sulfate.

Research has been ongoing in order to develop an effective method of inactivating prions.

SUMMARY

Surprisingly, it has been discovered that prions may be inactivated using a composition having a peracid alone, or a peracid and a surfactant despite traditional opinions that peracetic acid was ineffective, or had limited efficacy, against prions. The composition may be used to inactivate prions located on a variety of surfaces. The composition may include additional functional ingredients. The prions may be inactivated using a composition having a peracid alone, or a peracid and a surfactant in conjunction with higher temperatures.

These and other embodiments will be apparent to those of skill in the art and others in view of the following detailed description of some embodiments. It should be understood, however, that this summary, and the detailed description illustrate only some examples of various embodiments, and are not intended to be limiting to the invention as claimed.

DETAILED DESCRIPTION OF SOME EMBODIMENTS

As discussed above, the invention generally relates to a method of inactivating prions using a composition having a peracid alone, or a peracid and a surfactant. In certain embodiments, the composition may include additional functional ingredients. In certain embodiments, the method may be carried out using the composition in conjunction with elevated temperatures.

Surprisingly, it has been discovered that prions may be inactivated by applying a composition having a peracid alone, or a peracid and a surfactant to the prion. The term "inactivation" means that after treating the prion with the peracid composition, the prion is no longer capable of causing brain diseases including kuru, Creutzfeldt-Jakob disease, Gerstmann-Straussler-Scheinker disease, fatal familial insomnia, scrapie, bovine spongiform encephalopathy (Mad Cow Disease), transmissible mink encephalopathy, chronic wasting disease, feline spongiform encephalopathy, and similar brain diseases. The term "inactivation" also means that the prions cannot be visually detected using gel electrophoresis and Western blot analysis. It is understood that prions that cannot be visually detected using gel electrophoresis and Western blot analysis are not capable of causing the previously described brain diseases. The procedure used to test prions for inactivation is described in Appel et al., *J. Gen. Virology* (2001) 82, 465-473.

Definitions

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Weight percent, percent by weight, % by weight, wt %, and the like are synonyms that refer to the concentration of a substance as the weight of that substance divided by the weight of the composition and multiplied by 100.

The recitation of numerical ranges by endpoints includes all numbers subsumed within that range (e.g. 1 to 5 includes 1, 1.5, 2, 2.75, 3, 3.80, 4 and 5).

As used in this specification and the appended claims, the singular forms "a," "an," and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

The Peracid Composition

As discussed above, the peracid composition includes a peracid alone, or a peracid and a surfactant. The peracid composition may optionally include additional functional ingredients that enhance the effectiveness of the composition or provide an additional function or benefit. For example, the composition may include a complexing or sequestering agent, corrosion inhibitor, enzyme, optical brightener, defoamer, builder, enzyme stabilizing system, and the like.

The peracid composition may be a concentrate or a dilute solution. The concentrate refers to the composition that is diluted to form the use solution. The concentrate may be a solid, liquid, paste, gel, powder, tablet, or the like. The concentrate is preferably a powder or a liquid. The dilute solution or use solution refers to the composition that is applied to a surface to inactivate the prions. It may be beneficial to form the composition as a concentrate and dilute it to a use solution on-site. The concentrate is often easier and less expensive to ship than the use solution. When the concentrate is formed as a powder, the peracid is formed on-site once water is added and the composition reaches equilibrium.

When the peracid composition includes a surfactant, the peracid component and the surfactant component may be packaged together in one composition or may be packaged separately and combined at the point of use. Combining the peracid and the surfactant at the point of use may be desirable for surfactants that may not be compatible with the peracid over a period of time.

The pH of the concentrate composition may vary depending on the end use application and the physical form of the concentrate. The pH may be acidic, neutral or basic. For example, for a liquid composition that will be used to inactivate prions on clothing, the pH may range from about 1 to about 11, from about 1 to about 7, and from about 1 to about 4. For a powder composition that will be used to inactivate prions on clothing, the pH may range from about 9 to 12. For a powder composition to be used to inactivate prions on medical instruments or medical surfaces, the pH of the concentrate may range from about 1 to about 14, from about 7 to about 14, and from about 7 to about 13. A person skilled in the art will understand how to adjust the chemical formula to achieve the desired pH for the particular physical form and end use.

Peracid

The composition includes a "peracid," also referred to as a "peroxyacid." The peracid has a general formula of

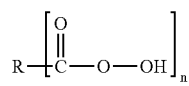

where R is an alkyl, arylalkyl, cycloalkyl, aromatic, or heteroaromatic group, and n is one or two. The R group may be linear or branched, having up to 12 carbon atoms. An arylalkyl group contains both aliphatic and aromatic structures. A cycloalkyl group is defined as a cyclic alkyl group.

Peracids useful in this invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxylactic, peroxymaleic, peroxyascorbic, peroxyhydroxyacetic, peroxyoxalic, peroxymalonic, peroxysuccinic, peroxyglutaric, peroxyadipic, peroxypimelic, and peroxysubric acid. The composition may include one peracid or a mixture of more than one peracid. The peracid is preferably peracetic acid with a structure of

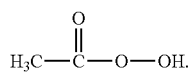

Typically, the peracid is formed in solution from a peracid precursor and an oxidizer. The resulting peracid exists in solution in equilibrium with the precursor and the oxidizer. The precursor is preferably tetracetylethylenediamine (TAED), or a carboxylic acid with a desired R group for the resulting peracid. The oxidizer is preferably hydrogen peroxide or perborate.

The concentrate should be formulated to provide the desired peracid concentration at equilibrium in the use solution. The peracid concentration at equilibrium in the use solution depends on factors such as the end use, the desired contact time, temperature, and the like. In one embodiment, the peracid concentration at equilibrium in the use solution may range from about 50 ppm to about 5000 ppm, from about 1000 ppm to about 3000 ppm, and from about 1500 ppm to about 2500 ppm. In another embodiment, the peracid concentration at equilibrium in the use solution may range from about 20 ppm to about 200 ppm, from about 40 ppm to about 100 ppm, and from about 50 ppm to about 90 ppm.

Surfactant

The composition includes a surfactant. The surfactant may be any surfactant including nonionic, anionic, amphoteric, and cationic surfactants. The surfactant is preferably compatible with the peracid component in that it does not render the peracid ineffective or unstable. The composition may include one surfactant or a mixture of more than one surfactant.

Useful anionic surfactants include the water soluble salts, preferably the alkali metal, ammonium and alkylolammonium salts, of organic sulfuric reaction products having in their molecular structure an alkyl group containing from about 10 to about 20 carbon atoms and a sulfonic acid or sulfuric acid ester group. (Included in the term "alkyl" is the alkyl portion of acyl groups.) Examples of this group of synthetic surfactants are the sodium and potassium alkyl sulfates, especially those obtained by sulfating the higher alcohols ($C_{12}$-$C_{18}$ carbon atoms) such as those produced by reducing the glycerides of tallow or coconut oil; and the sodium and potassium alkylbenzene sulfonates in which the alkyl group contains from about 10 to about 16 carbon atoms, in straight chain or branched chain configuration, e.g., see U.S. Pat. Nos. 2,220,099 and 2,477,383. Especially valuable are linear straight chain alkylbenzene sulfonates in which the average number of carbon atoms in the alkyl group is from about 11 to 14, abbreviated as $C_{11-14}$ LAS. Also, preferred are mixtures of $C_{10-16}$ (preferably $C_{11-13}$) linear alkylbenzene sulfonates and $C_{12-18}$ (preferably $C_{14-16}$) alkyl sulfates, alkyl ether sulfates, alcohol ethoxylate sulfates, etc.

Other anionic surfactants herein are the sodium alkyl glyceryl ether sulfonates, especially those ethers of higher alcohols derived from tallow and coconut oil; sodium coconut oil fatty acid monoglyceride sulfonates and sulfates; sodium or potassium salts of alkyl ethylene oxide ether sulfates containing from about 1 to about 10 units of ethylene oxide per molecule and wherein the alkyl groups contain from about 8 to about 12 carbon atoms; and sodium or potassium salts of alkyl ethylene oxide ether sulfates containing about 1 to about 10 units of ethylene oxide per molecule and wherein the alkyl group contains from about 10 to about 20 carbon atoms.

Other useful anionic surfactants herein include the water soluble salts of esters of alpha-sulfonated fatty acids containing from about 6 to 20 carbon atoms in the fatty acid group and from about 1 to 10 carbon atoms in the ester group; water soluble salts of 2-acyloxyalkane-1-sulfonic acids containing from about 2 to 9 carbon atoms in the acyl group and from about 9 to about 23 carbon atoms in the alkane moiety; water soluble salts of olefin and paraffin sulfonates containing from about 12 to 20 carbon atoms; and beta-alkyloxy alkane sulfonates containing from about 1 to 3 carbon atoms in the alkyl group and from about 8 to 20 carbon atoms in the alkane moiety.

Also useful are surface active substances which are categorized as anionics because the charge on the hydrophobe is negative; or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Of the cations (counterions) associated with these polar groups, sodium, lithium and potassium impart water solubility and are most preferred in compositions of the present invention.

Examples of suitable synthetic, water soluble anionic compounds are the alkali metal (such as sodium, lithium and potassium) salts or the alkyl mononuclear aromatic sulfonates such as the alkyl benzene sulfonates containing from about 5 to about 18 carbon atoms in the alkyl group in a straight or branched chain, e.g., the salts of alkyl benzene sulfonates or of alkyl naphthalene sulfonate, dialkyl naphthalene sulfonate and alkoxylated derivatives. Other anionic detergents are the olefin sulfonates, including long chain alkene sulfonates, long chain hydroxyalkane sulfonates or mixtures of alkenesulfonates and hydroxyalkane-sulfonates and alkylpoly (ethyleneoxy) ether sulfonates. Also included are the alkyl sulfates, alkyl poly (ethyleneoxy) ether sulfates and aromatic poly (ethyleneoxy) sulfates such as the sulfates or condensation products of ethylene oxide and nonyl phenol (usually having 1 to 6 oxyethylene groups per molecule).

Water soluble nonionic surfactants are also useful in the invention. Such nonionic materials include compounds produced by the condensation of alkylene oxide groups (hydrophilic in nature) with an organic hydrophobic group or compound, which may be aliphatic or alkyl in nature. The length of the polyoxyalkylene group which is condensed with any particular hydrophobic group can be readily adjusted to yield a water soluble compound having the desired degree of balance between hydrophilic and hydrophobic elements.

Included are the water soluble and water dispersible condensation products of aliphatic alcohols containing from 8 to 22 carbon atoms, in either straight chain or branched configuration, with from 3 to 12 moles of ethylene oxide per mole of alcohol. Nonionic surfactants are generally characterized by the presence of an organic hydrophobic group and an organic hydrophilic group and are typically produced by the condensation of an organic aliphatic, alkyl aromatic or polyoxyalkylene hydrophobic compound with a hydrophilic alkylene oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties.

Useful nonionic surfactants include block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available under the trade name PLURONIC® manufactured by BASF Corp. PLURONIC® compounds are difunctional (two reactive hydrogens) compounds formed by condensing ethylene oxide with a hydrophobic base formed by the addition of propylene oxide to two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule. TETRONIC® compounds are tetra-functional block copolymers derived from the sequential addition of propylene oxide and ethylene oxide to ethylenediamine. The molecular weight of the propylene oxide hydrotype ranges from about 500 to about 7,000; and, the hydrophile, ethylene oxide, is added to constitute from about 10% by weight to about 80% by weight of the molecule.

Also useful nonionic surfactants include the condensation products of one mole of alkyl phenol wherein the alkyl constituent, contains from about 8 to about 18 carbon atoms with from about 3 to about 50 moles of ethylene oxide. The alkyl group can, for example, be represented by diisobutylene, di-amyl, polymerized propylene, isoctyl, nonyl, and di-nonyl. Examples of commercial compounds of this chemistry are available on the market under the trade name IGEPAL® manufactured by Rhone-Poulenc and TRITON® manufactured by Union Carbide.

Likewise useful nonionic surfactants include condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range. Examples of like commercial surfactants are available under the trade name NEODOL® manufactured by Shell Chemical Co. and ALFONIC® manufactured by Vista Chemical Co. A class of nonionic surfactants are nonyl phenol ethoxylates, or NPE.

Condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above delineated carbon atoms range or it can consist of an acid having a specific number of carbon atoms within the range. Examples of commercial compounds of this chemistry are available on the market under the trade name NOPALCOL® manufactured by Henkel Corporation and LIPOPEG® manufactured by Lipo Chemicals, Inc. In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention. All of these ester moieties have one or more reactive hydrogen sites on their molecule which can undergo further acylation or ethylene oxide (alkoxide) addition to control the hydrophilicity of these substances.

Tertiary amine oxides corresponding to the general formula:

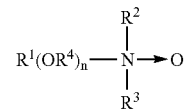

can be used wherein the →bond is a conventional representation of a semi-polar bond; and $R^1$, $R^2$, and $R^3$ may be aliphatic, aromatic, heterocyclic, alicyclic groups or a combination of such groups thereof. Generally, for amine oxides of detergent interest, $R^1$ is an alkyl radical of from about 8 to about 24 carbon atoms; $R^2$ and $R^3$ are selected from the group consisting of alkyl or hydroxyalkyl of 1-3 carbon atoms and mixtures thereof; $R^4$ is an alkylene or a hydroxyalkylene group containing 2 to 3 carbon atoms; and n ranges from 0 to about 20. Useful water soluble amine oxide surfactants are selected from the coconut or tallow dimethyl amine oxides.

Semi-polar nonionic surfactants include water soluble amine oxides containing one alkyl moiety of from about 10 to 18 carbon atoms and two moieties selected from the group of alkyl and hydroxyalkyl moieties of from about 1 to about 3 carbon atoms; water soluble phosphine oxides containing one alkyl moiety of about 10 to 18 carbon atoms and two moieties selected from the group consisting of alkyl groups and hydroxyalkyl groups containing from about 1 to 3 carbon atoms; and water soluble sulfoxides containing one alkyl moiety of from about 10 to 18 carbon atoms and a moiety selected from the group consisting of alkyl and hydroxylalkyl moieties of from about 1 to 3 carbon atoms. Nonionic surfactants are of the formula $R^1(OC_2H_4)_nOH$, wherein $R^1$ is a $C_6$-$C_{16}$ alkyl group and n is from 3 to about 80 can be used. Condensation products of $C_6$-$C_{15}$ alcohols with from about 5 to about 20 moles of ethylene oxide per mole of alcohol, e.g., $C_{12}$-$C_{14}$ alcohol condensed with about 6.5 moles of ethylene oxide per mole of alcohol.

Amphoteric surfactants include derivatives of aliphatic or aliphatic derivatives of heterocyclic secondary and tertiary amines in which the aliphatic moiety can be straight chain or branched and wherein one of the aliphatic substituents contain from about 8 to 18 carbon atoms and at least one aliphatic substituent contains an anionic water solubilizing group.

Cationic surfactants can also be included in the present invention. Cationic surfactants include a wide variety of compounds characterized by one or more organic hydrophobic groups in the cation and generally by a quaternary nitrogen associated with an acid radical. Pentavalent nitrogen ring compounds are also considered quaternary nitrogen compounds. Halides, methyl sulfate and hydroxide are suitable. Tertiary amines can have characteristics similar to cationic surfactants at washing solution pH values less than about 8.5. A more complete disclosure of these and other cationic surfactants useful herein can be found in U.S. Pat. No. 4,228,044, Cambre, issued Oct. 14, 1980, incorporated herein by reference.

Useful cationic surfactants also include those described in U.S. Pat. No. 4,222,905, Cockrell, issued Sep. 16, 1980, and in U.S. Pat. No. 4,239,659, Murphy, issued Dec. 16, 1980, both incorporated herein by reference.

As with the peracid concentration, the surfactant concentration in the use solution may vary depending on factors such as the end use, the desired contact time, temperature, and the like. For example, in one embodiment, the use solution composition at equilibrium may include from about 0.01 wt. % to about 10 wt. % surfactant, in an embodiment from about 0.01 wt. % to about 1 wt. % surfactant, and from about 0.01 wt. % to about 0.1 wt. % surfactant. In another embodiment, the use solution composition at equilibrium may include from about 0.1 wt. % to about 1 wt. % surfactant, in an embodiment from about 0.2 wt. % to about 0.8 wt. % surfactant, and in an embodiment from about 0.4 wt. % to about 0.6 wt. % surfactant.

Additional Functional Ingredients

Additional functional ingredients may optionally be used to improve the effectiveness of the composition or provide an additional function or benefit. Some non-limiting examples of such additional functional ingredients include the following: complexing or sequestering agents, corrosion inhibitors, enzymes, enzyme stabilizing systems, optical brighteners, builders, and defoamers.

Complexing or Sequestering Agents and Builders

The composition of the invention may optionally include a chelating agent, sequestering or complexing agent, or a builder. These ingredients generally provide cleaning properties and chelating properties. Exemplary detergent builders include sodium sulphate, sodium chloride, starch, sugars, $C_1$-$C_{10}$ alkylene glycols such as propylene glycol, and the like. Exemplary chelating agents include phosphates, phosphonates, and amino-acetates. Exemplary phosphates include sodium orthophosphate, potassium orthophosphate, sodium pyrophosphate, potassium pyrophosphate, sodium tripolyphosphate (STPP), and sodium hexametaphosphate. Exemplary phosphates include 1-hydroxyethane-1,1-diphosphonic acid, aminotrimethylene phosphonic acid, diethylenetriaminepenta(methylenephosphonic acid), 1-hydroxyethane-1,1-diphosphonic acid, $CH_3C(OH)[PO(OH)_2]_2$, aminotri(methylenephosphonic acid), $N[CH_2PO(OH_2)]_3$, aminotri(methylenephosphonate), sodium salt of

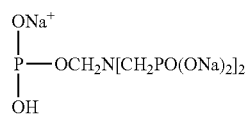

2-hydroxyethyliminobis(methylenephosphonic acid), $HOCH_2CH_2N[CH_2PO(OH)_2]_2$, diethylenetriaminepenta(methylenephosphonic acid), $(HO)_2POCH_2N[CH_2CH_2N[CH_2PO(OH)_2]_2]_2$, diethylenetriaminepenta(methylenephosphonate), sodium salt $C_9H_{(28-x)}N_3Na_xO_{15}P_5$ (x=7), hexamethylenediamine(tetramethylenephosphonate), potassium salt $C_{10}H_{(28-x)}N_2K_xO_{12}P_4$ (x=6), bis(hexamethylene)triamine(pentamethylenephosphonic acid) $(HO)_2POCH_2N[(CH_2)_6N[CH_2PO(OH)_2]_2]_2$, and phosphorous acid $H_3PO_3$. Exemplary amino-acetates include aminocarboxylic acids such as N-hydroxyethyliminodiacetic acid, nitrilotriacetic acid (NTA), ethylenediaminetetraacetic acid (EDTA), N-hydroxyethyl-ethylenediaminetriacetic acid (HEDTA), and diethylenetriaminepentaacetic acid (DTPA).

Corrosion Inhibitors

The composition may optionally include a corrosion inhibitor. A corrosion inhibitor provides compositions that generate surfaces that are shiner and less prone to biofilm buildup than surfaces that are not treated with compositions having a corrosion inhibitor. Preferred corrosion inhibitors which can be used according to the invention include phosphonates, phosphonic acids, triazoles, organic amines, sorbitan esters, carboxylic acid derivatives, sarcosinates, phosphate esters, zinc, nitrates, chromium, molybdate containing components, and borate containing components. Exemplary phosphates or phosphonic acids are available under the name Dequest (i.e., Dequest 2000, Dequest 2006, Dequest 2010, Dequest 2016, Dequest 2054, Dequest 2060, and Dequest 2066) from Solutia, Inc. of St. Louis, Mo. Exemplary triazoles are available under the name Cobratec (i.e., Cobratec 100, Cobratec TT-50-S, and Cobratec 99) from PMC Specialties Group, Inc. of Cincinnati, Ohio. Exemplary organic amines include aliphatic amines, aromatic amines, monoamines, diamines, triamines, polyamines, and their salts. Exemplary amines are available under the names Amp (i.e. Amp-95) from Angus Chemical Company of Buffalo Grove, Ill.; WGS (i.e., WGS-50) from Jacam Chemicals, LLC of Sterling, Kans.; Duomeen (i.e., Duomeen O and Duomeen C) from Akzo Nobel Chemicals, Inc. of Chicago, Ill.; DeThox amine (C Series and T Series) from DeForest Enterprises, Inc. of Boca Raton, Fla.; Deriphat series from Henkel Corp. of Ambler, Pa.; and Maxhib (AC Series) from Chemax, Inc. of Greenville, S.C. Exemplary sorbitan esters are available under the name Calgene (LA-series) from Calgene Chemical Inc. of Skokie, Ill. Exemplary carboxylic acid derivatives are available under the name Recor (i.e., Recor 12) from Ciba- Geigy Corp. of Tarrytown, N.Y. Exemplary sarcosinates are available under the names Hamposyl from Hampshire Chemical Corp. of Lexington, Mass.; and Sarkosyl from Ciba-Geigy Corp. of Tarrytown, N.Y.

The composition optionally includes a corrosion inhibitor for providing enhanced luster to the metallic portions of a surface. When a corrosion inhibitor is incorporated into the composition, it is preferably included in the concentrate in an amount of between about 0.05 wt. % and about 25 wt. %, between about 0.5 wt. % and about 20 wt. % and between about 1 wt. % and about 15 wt. %.

Enzymes

The composition of the present invention may optionally include one or more enzymes, which can provide desirable activity for removal of protein-based, carbohydrate-based, or triglyceride-based soil from substrates. Although not limiting to the present invention, enzymes suitable for the compositions can act by degrading or altering one or more types of soil residues encountered on a surface or textile thus removing the soil or making the soil more removable by a surfactant or other component of the cleaning composition. Both degradation and alteration of soil residues can improve detergency by reducing the physicochemical forces which bind the soil to the surface or textile being cleaned, i.e. the soil becomes more water soluble. For example, one or more proteases can cleave complex, macromolecular protein structures present in soil residues into simpler short chain molecules which are, of themselves, more readily desorbed from surfaces, solubilized or otherwise more easily removed by detersive solutions containing said proteases.

Suitable enzymes include a protease, an amylase, a lipase, a gluconase, a cellulase, a peroxidase, or a mixture thereof of any suitable origin, such as vegetable, animal, bacterial, fungal or yeast origin. Preferred selections are influenced by factors such as pH-activity and/or stability optima, thermostability, and stability to active detergents, builders and the like. In this respect bacterial or fungal enzymes are preferred, such as bacterial amylases and proteases, and fungal cellulases. Preferably the enzyme is a protease, a lipase, an amylase, or a combination thereof.

"Detersive enzyme", as used herein, means an enzyme having a cleaning, destaining or otherwise beneficial effect as a component of a composition.

Enzymes are normally incorporated into a composition according to the invention in an amount sufficient to yield effective cleaning during a washing or presoaking procedure. An amount effective for cleaning refers to an amount that produces a clean, sanitary, and, preferably, corrosion free appearance to the material cleaned. An amount effective for cleaning also can refer to an amount that produces a cleaning, stain removal, soil removal, whitening, deodorizing, or freshness improving effect on substrates. Typically such a cleaning effect can be achieved with amounts of enzyme from about 0.1% to about 3% by weight, preferably about 1% to about 3% by weight, of the composition. Higher active levels may also be desirable in highly concentrated cleaning or presoak formulations. A presoak is preferably formulated for use upon a dilution of about 1:500, or to a formulation concentration of 2000 ppm, which puts the use concentration of the enzyme at about 10 to about 30 ppm.

Commercial enzymes, such as alkaline proteases, are obtainable in liquid or dried form, are sold as raw aqueous solutions or in assorted purified, processed and compounded forms, and include about 2% to about 80% by weight active enzyme generally in combination with stabilizers, buffers, cofactors, impurities and inert vehicles. The actual active enzyme content depends upon the method of manufacture and is not critical, assuming the composition has the desired enzymatic activity. The particular enzyme chosen for use in the process and products of this invention depends upon the conditions of final utility, including the physical product form, use pH, use temperature, and soil types to be degraded or altered. The enzyme can be chosen to provide optimum activity and stability for any given set of utility conditions.

A valuable reference on enzymes is "Industrial Enzymes", Scott, D., in *Kirk-Othmer Encyclopedia of Chemical Technology*, 3rd Edition, (editors Grayson, M. and EcKroth, D.) Vol. 9, pp. 173-224, John Wiley & Sons, New York, 1980.

Protease

A protease suitable for the composition of the present invention can be derived from a plant, an animal, or a microorganism. Preferably the protease is derived from a microorganism, such as a yeast, a mold, or a bacterium. Preferred proteases include serine proteases active at alkaline pH, preferably derived from a strain of *Bacillus* such as *Bacillus subtilis* or *Bacillus licheniformis*; these preferred proteases include native and recombinant subtilisins. The protease can be purified or a component of a microbial extract, and either wild type or variant (either chemical or recombinant). A preferred protease is neither inhibited by a metal chelating agent (sequestrant) or a thiol poison nor activated by metal ions or reducing agents, has a broad substrate specificity, is inhibited by diisopropylfluorophosphate (DFP), is an endopeptidase, has a molecular weight in the range of about 20,000 to about 40,000, and is active at a pH of about 6 to about 12 and at temperatures in a range from about 20° C. to about 80° C.

Examples of proteolytic enzymes which can be employed in the composition of the invention include (with trade names) Savinase®; a protease derived from *Bacillus lentus* type, such as Maxacal®, Opticlean®, Durazym®, and Properase®; a protease derived from *Bacillus licheniformis*, such as Alcalase® and Maxatase®; and a protease derived from *Bacillus amyloliquefaciens*, such as Primase®. Preferred commercially available protease enzymes include those sold under the trade names Alcalase®, Savinase®, Primase®, Durazym®, or Esperase® by Novo Industries A/S (Denmark); those sold under the trade names Maxatase®, Maxacal®, or Maxapem® by Gist-Brocades (Netherlands); those sold under the trade names Purafect®, Purafect OX, and Properase by Genencor International; those sold under the trade names Opticlean® or Optimase® by Solvay Enzymes; and the like. A mixture of such proteases can also be used. For example, Purafect® is a preferred alkaline protease (a subtilisin) for use in compositions of this invention having application in lower temperature cleaning programs, from about 30° C. to about 65° C.; whereas, Esperase® is an alkaline protease of choice for higher temperature detersive solutions, from about 50° C. to about 85° C. Suitable detersive proteases are described in patent publications including: GB 1,243,784, WO 9203529 A (enzyme/inhibitor system), WO 9318140 A, and WO 9425583 (recombinant trypsin-like protease) to Novo; WO 9510591 A, WO 9507791 (a protease having decreased adsorption and increased hydrolysis), WO 95/30010, WO 95/30011, WO 95/29979, to Procter & Gamble; WO 95/10615 (*Bacillus amyloliquefaciens* subtilisin) to Genencor International; EP 130,756 A (protease A); EP 303,761 A (protease B); and EP 130,756 A. A variant protease employed in the present compositions is preferably at least 80% homologous, preferably having at least 80% sequence identity, with the amino acid sequences of the proteases in these references.

In preferred embodiments of this invention, the amount of commercial alkaline protease composite present in the composition of the invention ranges from about 0.1% by weight of detersive solution to about 3% by weight, preferably about 1% to about 3% by weight, preferably about 2% by weight, of solution of the commercial enzyme product. Typical commercially available detersive enzymes include about 5-10% of active enzyme.

Whereas establishing the percentage by weight of commercial alkaline protease required is of practical convenience for manufacturing embodiments of the present teaching, variance in commercial protease concentrates and in-situ environmental additive and negative effects upon protease activity require a more discerning analytical technique for protease assay to quantify enzyme activity and establish correlations to soil residue removal performance and to enzyme stability within the preferred embodiment; and, if a concentrate, to use-dilution solutions. The activity of the proteases for use in the present invention are readily expressed in terms of activity units—more specifically, Kilo-Novo Protease Units (KNPU) which are azocasein assay activity units well known to the art. A more detailed discussion of the azocasein assay procedure can be found in the publication entitled "The Use of Azoalbumin as a Substrate in the Colorimetric Determination of Peptic and Tryptic Activity", Tomarelli, R. M., Charney, J., and Harding, M. L., *J. Lab. Clin. Chem.* 34,428 (1949).

In preferred embodiments of the present invention, the activity of proteases present in the use-solution ranges from about $1\times10^{-5}$ KNPU/gm solution to about $4\times10^{-3}$ KNPU/gm solution.

Naturally, mixtures of different proteolytic enzymes may be incorporated into this invention. While various specific enzymes have been described above, it is to be understood that any protease which can confer the desired proteolytic activity to the composition may be used and this embodiment of this invention is not limited in any way by specific choice of proteolytic enzyme.

Amylase

An amylase suitable for the composition of the present invention can be derived from a plant, an animal, or a microorganism. Preferably the amylase is derived from a microorganism, such as a yeast, a mold, or a bacterium. Preferred amylases include those derived from a *Bacillus*, such as *B. licheniformis, B. amyloliquefaciens, B. subtilis*, or *B. stearothermophilus*. The amylase can be purified or a component of a microbial extract, and either wild type or variant (either chemical or recombinant), preferably a variant that is more stable under washing or presoak conditions than a wild type amylase.

Examples of amylase enzymes that can be employed in the composition of the invention include those sold under the trade name Rapidase by Gist-Brocades® (Netherlands); those sold under the trade names Termamyl®, Fungamyl® or Duramyl® by Novo; Purastar STL or Purastar OXAM by Genencor; and the like. Preferred commercially available amylase enzymes include the stability enhanced variant amylase sold under the trade name Duramyl® by Novo. A mixture of amylases can also be used.

Amylases suitable for the compositions of the present invention include: I-amylases described in WO 95/26397, PCT/DK96/00056, and GB 1,296,839 to Novo; and stability enhanced amylases described in J. Biol. Chem., 260(11): 6518-6521 (1985); WO 9510603 A, WO 9509909 A and WO 9402597 to Novo; references disclosed in WO 9402597; and WO 9418314 to Genencor International. A variant I-amylase employed in the present compositions is preferably at least 80% homologous, preferably having at least 80% sequence identity, with the amino acid sequences of the proteins of these references.

Preferred amylases for use in the compositions of the present invention have enhanced stability compared to certain amylases, such as Termamyl®. Enhanced stability refers to a significant or measurable improvement in one or more of: oxidative stability, e.g., to hydrogen peroxide/tetraacetylethylenediamine in buffered solution at pH 9-10; thermal stability, e.g., at common wash temperatures such as about 60° C.; and/or alkaline stability, e.g., at a pH from about 8 to about 11; each compared to a suitable control amylase, such as Termamyl®. Stability can be measured by methods known to those of skill in the art. Preferred enhanced stability amylases for use in the compositions of the present invention have a specific activity at least 25% higher than the specific activity of Termamyl® at a temperature in a range of 25° C. to 55° C. and at a pH in a range of about 8 to about 10. Amylase activity for such comparisons can be measured by assays known to those of skill in the art and/or commercially available, such as the Phadebas® I-amylase assay.

In preferred embodiments of this invention, the amount of commercial amylase present in the composition of the invention ranges from about 0.1% by weight of detersive solution to about 3% by weight, preferably about 1% to about 3% by weight, preferably about 2% by weight, of solution of the commercial enzyme product. Typical commercially available detersive enzymes include about 0.25-5% of active amylase.

Whereas establishing the percentage by weight of amylase required is of practical convenience for manufacturing embodiments of the present teaching, variance in commercial amylase concentrates and in-situ environmental additive and negative effects upon amylase activity may require a more discerning analytical technique for amylase assay to quantify enzyme activity and establish correlations to soil residue removal performance and to enzyme stability within the preferred embodiment; and, if a concentrate, to use-dilution solutions. The activity of the amylases for use in the present invention can be expressed in units known to those of skill or through amylase assays known to those of skill in the art and/or commercially available, such as the Phadebas® I-amylase assay.

Naturally, mixtures of different amylase enzymes can be incorporated into this invention. While various specific enzymes have been described above, it is to be understood that any amylase which can confer the desired amylase activity to the composition can be used and this embodiment of this invention is not limited in any way by specific choice of amylase enzyme.

Cellulases

A cellulase suitable for the composition of the present invention can be derived from a plant, an animal, or a microorganism. Preferably the cellulase is derived from a microorganism, such as a fungus or a bacterium. Preferred cellulases include those derived from a fungus, such as *Humicola insolens, Humicola* strain DSM1800, or a cellulase 212-producing fungus belonging to the genus *Aeromonas* and those extracted from the hepatopancreas of a marine mollusk, *Dolabella Auricula Solander*. The cellulase can be purified or a component of an extract, and either wild type or variant (either chemical or recombinant).

Examples of cellulase enzymes that can be employed in the composition of the invention include those sold under the trade names Carezyme® or Celluzyme® by Novo, or Cellulase by Genencor; and the like. A mixture of cellulases can also be used. Suitable cellulases are described in patent documents including: U.S. Pat. No. 4,435,307, GB-A-2.075.028, GB-A-2.095.275, DE-OS-2.247.832, WO 9117243, and WO 9414951 A (stabilized cellulases) to Novo.

In preferred embodiments of this invention, the amount of commercial cellulase present in the composition of the invention ranges from about 0.1% by weight of detersive solution to about 3% by weight, preferably about 1% to about 3% by weight, of solution of the commercial enzyme product. Typical commercially available detersive enzymes include about 5-10 percent of active enzyme.

Whereas establishing the percentage by weight of cellulase required is of practical convenience for manufacturing embodiments of the present teaching, variance in commercial cellulase concentrates and in-situ environmental additive and negative effects upon cellulase activity may require a more discerning analytical technique for cellulase assay to quantify enzyme activity and establish correlations to soil residue removal performance and to enzyme stability within the preferred embodiment; and, if a concentrate, to use-dilution solutions. The activity of the cellulases for use in the present invention can be expressed in units known to those of skill or through cellulase assays known to those of skill in the art and/or commercially available.

Naturally, mixtures of different cellulase enzymes can be incorporated into this invention. While various specific enzymes have been described above, it is to be understood that any cellulase which can confer the desired cellulase activity to the composition can be used and this embodiment of this invention is not limited in any way by specific choice of cellulase enzyme.

Lipases

A lipase suitable for the composition of the present invention can be derived from a plant, an animal, or a microorganism. Preferably the lipase is derived from a microorganism, such as a fungus or a bacterium. Preferred lipases include those derived from a *Pseudomonas*, such as *Pseudomonas stutzeri* ATCC 19.154, or from a *Humicola*, such as *Humicola lanuginosa* (typically produced recombinantly in *Aspergillus oryzae*). The lipase can be purified or a component of an extract, and either wild type or variant (either chemical or recombinant).

Examples of lipase enzymes that can be employed in the compositions of the invention include those sold under the trade names Lipase P "Amano" or "Amano-P" by Amano Pharmaceutical Co. Ltd., Nagoya, Japan or under the trade name Lipolase® by Novo, and the like. Other commercially available lipases that can be employed in the present compositions include Amano-CES, lipases derived from *Chromobacter viscosum*, e.g. *Chromobacter viscosum* var. *lipolyticum* NRRLB 3673 from Toyo Jozo Co., Tagata, Japan; *Chromobacter viscosum* lipases from U.S. Biochemical Corp., U.S.A. and Disoynth Co., and lipases derived from *Pseudomonas gladioli* or from *Humicola lanuginosa*.

A preferred lipase is sold under the trade name Lipolase® by Novo. Suitable lipases are described in patent documents including: WO 9414951 A (stabilized lipases) to Novo, WO 9205249, RD 94359044, GB 1,372,034, Japanese Patent Application 53,20487, laid open Feb. 24, 1978 to Amano Pharmaceutical Co. Ltd., and EP 341,947.

In preferred embodiments of this invention, the amount of commercial lipase present in the composition of the invention ranges from about 0.1% by weight of detersive solution to about 3% by weight, preferably about 1% to about 3% by weight, of solution of the commercial enzyme product. Typical commercially available detersive enzymes include about 5-10 percent of active enzyme.

Whereas establishing the percentage by weight of lipase required is of practical convenience for manufacturing embodiments of the present teaching, variance in commercial lipase concentrates and in-situ environmental additive and negative effects upon lipase activity may require a more discerning analytical technique for lipase assay to quantify enzyme activity and establish correlations to soil residue removal performance and to enzyme stability within the preferred embodiment; and, if a concentrate, to use-dilution solutions. The activity of the lipases for use in the present invention can be expressed in units known to those of skill or through lipase assays known to those of skill in the art and/or commercially available.

Naturally, mixtures of different lipase enzymes can be incorporated into this invention. While various specific enzymes have been described above, it is to be understood that any lipase which can confer the desired lipase activity to the composition can be used and this embodiment of this invention is not limited in any way by specific choice of lipase enzyme.

Additional Enzymes

Additional enzymes suitable for use in the present compositions include a cutinase, a mannanase, a peroxidase, a gluconase, and the like. Suitable cutinase enzymes are described in WO 8809367 A to Genencor. Known peroxidases include horseradish peroxidase, ligninase, and haloperoxidases such as chloro- or bromo-peroxidase. Peroxidases suitable for compositions are disclosed in WO 89099813 A and WO 8909813 A to Novo. Peroxidase enzymes can be used in combination with oxygen sources, e.g., percarbonate, perborate, hydrogen peroxide, and the like. Additional enzymes suitable for incorporation into the present composition are disclosed in WO 9307263 A and WO 9307260 A to Genencor International, WO 8908694 A to Novo, and U.S. Pat. No. 3,553,139 to McCarty et al., U.S. Pat. No. 4,101,457 to Place et al., U.S. Pat. No. 4,507,219 to Hughes and U.S. Pat. No. 4,261,868 to Hora et al.

An additional enzyme, such as a cutinase or peroxidase, suitable for the composition of the present invention can be derived from a plant, an animal, or a microorganism. Preferably the enzyme is derived from a microorganism. The enzyme can be purified or a component of an extract, and either wild type or variant (either chemical or recombinant). In preferred embodiments of this invention, the amount of commercial additional enzyme, such as a cutinase or peroxidase, present in the composition of the invention ranges from about 0.1% by weight of detersive solution to about 3% by weight, preferably about 1% to about 3% by weight, of solution of the commercial enzyme product. Typical commercially available detersive enzymes include about 5-10 percent of active enzyme.

Whereas establishing the percentage by weight of additional enzyme, such as a cutinase or peroxidase, required is of practical convenience for manufacturing embodiments of the present teaching, variance in commercial additional enzyme concentrates and in-situ environmental additive and negative effects upon their activity may require a more discerning analytical technique for the enzyme assay to quantify enzyme activity and establish correlations to soil residue removal performance and to enzyme stability within the preferred embodiment; and, if a concentrate, to use-dilution solutions. The activity of the additional enzyme, such as a cutinase or peroxidase, for use in the present invention can be expressed in units known to those of skill or through assays known to those of skill in the art and/or commercially available.

Naturally, mixtures of different additional enzymes can be incorporated into this invention. While various specific enzymes have been described above, it is to be understood that any additional enzyme which can confer the desired enzyme activity to the composition can be used and this embodiment of this invention is not limited in any way by specific choice of enzyme.

In addition to including enzyme, the compositions of the invention may include an enzyme stabilizing system to help maintain enzyme activity over time.

Optical Brighteners

Optical brighteners are also referred to as fluorescent whitening agents or fluorescent brightening agents. Optical brighteners for example provide optical compensation for the yellow cast in fabric substrates. With optical brighteners, yellowing is replaced by light emitted from optical brighteners present in the area commensurate in scope with yellow color. The violet to blue light supplied by the optical brighteners combines with other light reflected from the location to provide a substantially complete or enhanced bright white appearance. This additional light is produced by the brightener through fluorescence. Optical brighteners absorb light in the ultraviolet range 275 through 400 nm. and emit light in the ultraviolet blue spectrum 400-500 nm.

Fluorescent compounds belonging to the optical brightener family are typically aromatic or aromatic heterocyclic materials often containing condensed ring system. An important feature of these compounds is the presence of an uninterrupted chain of conjugated double bonds associated with an aromatic ring. The number of such conjugated double bonds is dependent on substituents as well as the planarity of the fluorescent part of the molecule. Most brightener compounds are derivatives of stilbene or 4,4'-diamino stilbene, biphenyl, five membered heterocycles (triazoles, oxazoles, imidazoles, etc.) or six membered heterocycles (cumarins, naphthalamides, triazines, etc.).

Optical brighteners useful in the present invention are commercially available and will be appreciated by those skilled in the art. Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles and other miscellaneous agents. Examples of these types of brighteners are disclosed in "The Production and Application of Fluorescent Brightening Agents", M. Zahradnik, Published by John Wiley & Sons, New York (1982), the disclosure of which is incorporated herein by reference.

Foam Inhibitors or Defoamers

A foam inhibitor may be included for reducing the stability of any foam that is formed. Examples of foam inhibitors include silicon compounds such as silica dispersed in polydimethylsiloxane, fatty amides, hydrocarbon waxes, fatty acids, fatty esters, fatty alcohols, fatty acid soaps, ethoxylates, mineral oils, polyethylene glycol esters, polyoxyethylene-polyoxypropylene block copolymers, alkyl phosphate esters such as monostearyl phosphate and the like. A discussion of foam inhibitors may be found, for example, in U.S. Pat. No. 3,048,548 to Martin et al., U.S. Pat. No. 3,334,147 to Brunelle et al., and U.S. Pat. No. 3,442,242 to Rue et al., the disclosures of which are incorporated by reference herein. The composition preferably includes from about 0.0001 wt. % to about 5 wt. % and more preferably from about 0.01 wt. % to about 3 wt. % of the foam inhibitor.

Methods of Using the Composition

When applied to a surface, in an embodiment the peracid composition is applied to the surface for at least about 1 minute, in an embodiment for at least about 15 minutes, and in an embodiment for at least about 30 minutes.

The peracid composition alone may be applied to a surface at room temperature or about 10° C. to about 30° C. (about 50° F. to about 85° F.). The peracid composition may optionally be used in conjunction with heat. When the peracid composition is used in conjunction with heat, the temperature of the peracid composition while applied to a surface is at least about 30° C. for at least about 1 minute, at least about 15 minutes, or at least about 30 minutes. The temperature of the peracid composition may be at least about 80° C. for at least about 1 minute, at least about 10 minutes, or at least about 15 minutes.

The peracid composition may be used to inactivate prions on any surface contaminated with prions. For example, the peracid composition may be used to inactivate prions on surfaces in a slaughterhouse such as meat slicers, cutting boards, environmental surfaces such as floors and walls, and slaughterhouse equipment; surfaces in the food processing industry and the meat industry in particular such as meat slicers, cutting boards, environmental surfaces such as floors and walls, knives, and other instruments typically found in the food processing or meat industries; surfaces in a kitchen such as knives, cutting boards, meat slicers, floors, walls, and the like; surfaces in a hospital, nursing home, dental facility, surgical center, and the like such as medical equipment, endoscopes, surgical instruments especially dedicated instruments for brain and eye surgery, and lymphatic tissue, the environment such as floors, walls and the like; laundry such as hospital linens, operating theatre textiles, clothes worn on a farm, in a slaughterhouse, in a medical facility, or any other location where prions may be encountered; and food and meat surfaces such as animal carcass, and cut meat prior to packaging.

The peracid composition may be used to inactivate a variety of prions including prions responsible for causing brain diseases such as kuru, Creutzfeldt-Jakob disease, Gerstmann-Straussler-Scheinker disease, fatal familial insomnia, scrapie, bovine spongiform encephalopathy (Mad Cow Disease), transmissible mink encephalopathy, chronic wasting disease, and feline spongiform encephalopathy. The peracid composition may be used to inactivate more than one prion.

For a more complete understanding of the invention, the following examples are given to illustrate some embodiment. These examples and experiments are to be understood as illustrative and not limiting. All parts are by weight, except where it is contrarily indicated.

EXAMPLES

The following formulas are examples of compositions of the invention. These formulas, and other compositions envisioned by the present invention, may be tested against prions using the methods known to a person skilled in the art including gel electrophoresis and Western blot test methods and the methods described in Appel et al., *J. Gen. Virology* (2001) 82, 465-473.

| Formula 1 | | Formula 2 | | Formula 3 | |
|---|---|---|---|---|---|
| 55.7% | Sodium Carbonate | 20.3% | Hydrogen Peroxide | 50.0% | Sodium Per Borate |
| 18.7% | Sodium Metasilicate | 12.0% | Acetic Acid | | |
| 7.0% | Alcohol Ethoxylate ($C_{13}$–$C_{15}$) 7 EO | 9.0% | Peracetic Acid | 25.0% | Tetraacetylethylenediamine |
| 4.5% | Maleic Acid/Acrylic Acid Copolymer | 0.6% | 1-hydroxyethylidene-1,1-diphosphonic acid | 22.15% | Citric Acid |
| | | | | 0.10% | Benzotriazole |
| 4.3% | Nitrilotriacetic Acid (NTA) | Balance | Water | 0.05% | Sodium salt of diethylene triamine penta(methylene phosphoric acid) |
| 1.3% | Sodium Alkylbenzenesulfonate | | | | |
| 1.2% | 1-hydroxyethylidene-1,1-diphosphonic acid | | | 2.0% | $C_{10}$–$C_{14}$ alcohol ethyoxylate (6 EO) |
| 0.96% | Carboxymethylcellulose | | | | |
| 0.7% | Protease | | | | |
| 0.2% | Stilbentriazine-derivative (Tinopal DMS/X commercially available from Ciba) | | | | |
| 0.16% | 0.14% paraffin wax and 0.06% silicone oil | | | | |
| Balance | Water and raw material salts | | | | |

The compositions of the present invention are believed to be effective at reducing the number of active prions on a surface by at least about 1.5 logs and preferably at least about 3 logs. When using Western blot technology, the absence of staining is believed to indicate the absence of active prion protein. This log reduction may be determined by comparing a gel with prion treated with a composition of the invention and diluted in serial log dilutions to a gel with prion treated only with buffer and diluted in serial log reductions.

The foregoing summary, detailed description, and examples provide a sound basis for understanding the invention, and some specific example embodiments of the invention. Since the invention can comprise a variety of embodiments, the above information is not intended to be limiting. The invention resides in the claims.

What is claimed is:

1. A method of inactivating a prion located on a surface comprising:

applying to the surface a composition consisting of:

a peracid precursor consisting of acetic acid and octanoic acid;

hydrogen peroxide;

peracetic acid;

peroctanoic acid;

a nonionic surfactant;

a chelating agent;

water; and optionally an additional functional ingredient, wherein the peracid concentration at equilibrium in the composition is about 20 ppm to about 200 ppm; and maintaining the composition at least about 30° C. for at least about 1 minute, the composition being effective at inactivating a prion capable of causing a brain disease selected from the group consisting of kuru, Creutzfeldt-Jakob disease, Gerstmann-Straussler-Scheiniker disease, fatal familial insomnia, scrapie, bovine spongiform encephalopathy, transmissible mink encephalopathy, chronic wasting disease, and feline spongiform encephalopathy, and the composition being capable of decreasing the number of the prions in a container by at least about 3 logs.

2. The method of claim 1, wherein the surface is selected from the group consisting of a meat slicer, a cutting board, a floor, a wall, a knife, a surgical instrument, a textile, and a food surface.

3. The method of claim 1, wherein the additional functional ingredient is selected from the group consisting of a complexing agent, a sequestering agent, a builder, an enzyme, an enzyme stabilizing system, a defoamer, a foam inhibitor, an optical brightener, a corrosion inhibitor, and mixture thereof.

4. A method of treating a surface comprising:

applying to the surface a composition consisting of:

a peracid precursor consisting of acetic acid and octanoic acid;

hydrogen peroxide;

peracetic acid;

peroctanoic acid;

a nonionic surfactant;

a chelating agent; and water; wherein the peracid concentration at equilibrium in the composition is about 20 ppm to about 200 ppm and maintaining the composition at least about room temperature for at least about 1 minute, the composition being effective at inactivating a prion capable of causing a brain disease selected from the group consisting of kuru, Creutzfeldt-Jakob disease, Gerstmann-Straussler-Scheiniker disease, fatal familial insomnia, scrapie, bovine spongiform encephalopathy, transmissible mink encephalopathy, chronic wasting disease, and feline spongiform encephalopathy, and the composition being capable of decreasing the number of the prions in a container by at least about 1.5 logs.

* * * * *